US008527617B2

(12) United States Patent
Nakano

(10) Patent No.: US 8,527,617 B2
(45) Date of Patent: Sep. 3, 2013

(54) MEDICAL DIAGNOSTIC APPARATUS, MEDICAL NETWORK SYSTEM, AND METHOD OF CONTROLLING MEDICAL DIAGNOSTIC APPARATUS

(75) Inventor: Kenshi Nakano, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1521 days.

(21) Appl. No.: 11/560,208

(22) Filed: Nov. 15, 2006

(65) Prior Publication Data

US 2007/0118635 A1 May 24, 2007

Related U.S. Application Data

(63) Continuation of application No. PCT/JP2006/306934, filed on Mar. 31, 2006.

(30) Foreign Application Priority Data

Mar. 31, 2005 (JP) ................................. 2005-101157

(51) Int. Cl.
 *G06F 15/173* (2006.01)
(52) U.S. Cl.
 USPC ............ 709/223; 382/128; 600/437; 717/120
(58) Field of Classification Search
 USPC ................ 709/219, 223; 382/128; 600/437; 717/120
 See application file for complete search history.

(56) References Cited

U.S. PATENT DOCUMENTS

| 6,289,115 | B1* | 9/2001 | Takeo ........................... 382/130 |
| 2002/0023172 | A1 | 2/2002 | Gendron et al. |
| 2004/0215490 | A1* | 10/2004 | Duchon et al. .................... 705/2 |
| 2005/0043828 | A1* | 2/2005 | Tanaka et al. ................... 700/83 |
| 2005/0097191 | A1* | 5/2005 | Yamaki et al. ................ 709/219 |

FOREIGN PATENT DOCUMENTS

| EP | 1 336 378 A1 | 8/2003 |
| JP | 11-239165 | 8/1999 |
| JP | 2002-177238 | 6/2002 |
| JP | 2002-259242 | 9/2002 |
| JP | 2003-116154 | 4/2003 |
| JP | 2004-337503 | 12/2004 |

OTHER PUBLICATIONS

Office Action issued Sep. 8, 2010, in Japan Patent Application No. 2005-101157 (with English translation).
European Office Action issued Dec. 18, 2012 in Patent Application No. 06730882.5.

* cited by examiner

*Primary Examiner* — Asad Nawaz
*Assistant Examiner* — Najeebuddin Ansari
(74) *Attorney, Agent, or Firm* — Oblon, Spivak, McClelland, Maier & Neustadt, L.L.P.

(57) ABSTRACT

When an ultrasonic diagnostic apparatus is connected to an HIS/RIS server, a PACS server, and an imager through a hospital network, the state of communication or connection with the HIS/RIS server, the PACS server, and the imager is determined using information stored in a common system designing table. In addition, the ultrasonic diagnostic apparatus sends communication line opening requests to the HIS/RIS server, the PACS server, and the imager, and determines a DICOM service and a transfer syntax, which are supported by each destination, on the basis of the responses to the communication line opening requests so as to store information in an intrinsic system designing table.

7 Claims, 5 Drawing Sheets

FIG. 2

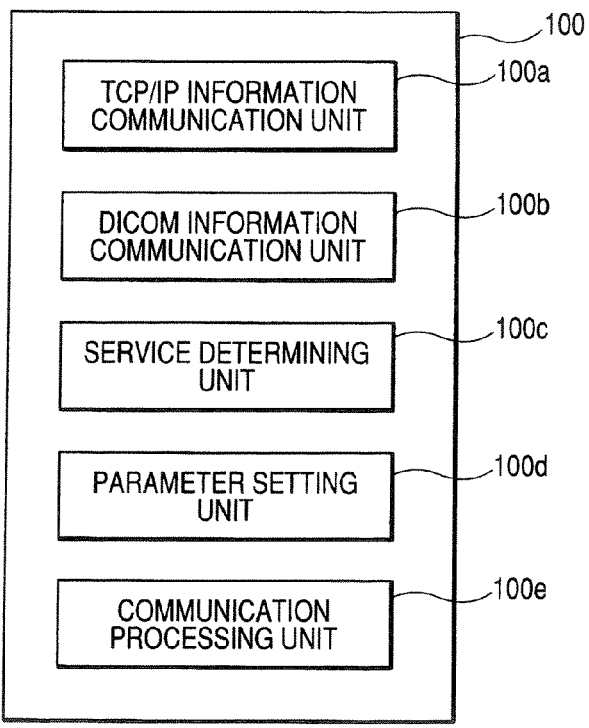

FIG. 3A

| HOST | IP ADDRESS | AE TITLE | PORT NUMBER |
|---|---|---|---|
| HIS/RIS | 192.168.0.2 | RIS | 104 |
| IMAGER | 192.168.0.4 | PRINTER | 106 |
| SERVER | 192.168.0.5 | SERVER | 106 |

FIG. 3B

| AE TITLE | ABSTRACT SYNTAX | TRANSFER SYNTAX |
|---|---|---|
| RIS | MODALITY WORKLIST FIND | IMPLICIT VR LITTLE ENDIAN |
| SERVER | ULTRASONIC IMAGE STORAGE | IMPLICIT VR LITTLE ENDIAN |
| | | EXPLICIT VR LITTLE ENDIAN |
| | | JPEG BASELINE PROCESS 1 |
| | ULTRASONIC MULTI-FRAME IMAGE STORAGE | JPEG BASELINE PROCESS 1 |
| IMAGER | BASIC GRAYSCALE PRINT MANAGEMENT | EXPLICIT VR LITTLE ENDIAN |

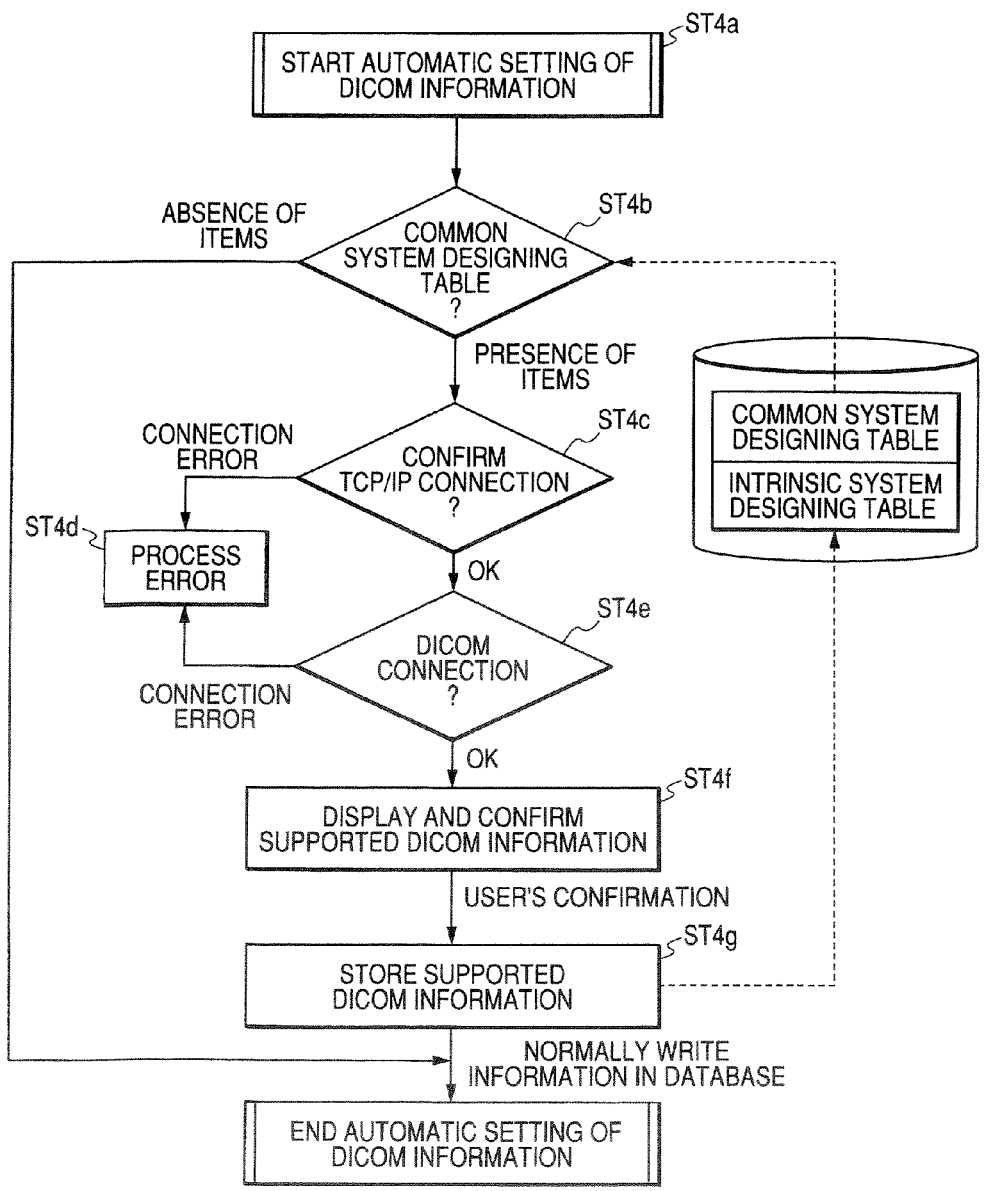

FIG. 6

| HOST NAME | IP ADDRESS | AE TITLE | HOST NUMBER | ABSTRACT SYNTAX | TRANSFER SYNTAX |
|---|---|---|---|---|---|
| HIS/RIS | 192.168.0.3 | RIS | 104 | MODALITY WORKLIST FIND | IMPLICIT VR LITTLE ENDIAN |
|  |  |  | 105 | MODALITY PPS | IMPLICIT VR LITTLE ENDIAN |
| SERVER | 192.168.0.5 | SERVER | 107 | ULTRASONIC IMAGE STORAGE | IMPLICIT VR LITTLE ENDIAN |
|  |  |  |  |  | EXPLICIT VR LITTLE ENDIAN |
|  |  |  |  | ULTRASONIC MULTI-FRAME IMAGE STORAGE | JPEG BASELINE PROCESS 1 |
|  |  |  |  |  | JPEG BASELINE PROCESS 1 |
| IMAGER | 192.168.0.4 | PRINTER | 106 | BASIC GRAYSCALE PRINT MANAGEMENT | IMPLICIT VR LITTLE ENDIAN |

MEDICAL DIAGNOSTIC APPARATUS, MEDICAL NETWORK SYSTEM, AND METHOD OF CONTROLLING MEDICAL DIAGNOSTIC APPARATUS

CROSS REFERENCE TO RELATED APPLICATIONS

This is a Continuation Application of PCT Application No. PCT/JP2006/306934, filed Mar. 31, 2006, which was published under PCT Article 21(2) in Japanese.

This application is based upon and claims the benefit of priority from prior Japanese Patent Application No. 2005-101157, filed Mar. 31, 2005, the entire contents of which are incorporated herein by reference.

BACKGROUND OF THE INVENTION

1. Field of the Invention

The present invention relates to a medical diagnostic apparatus that can be connected to various medical devices through a network and control services supported by the various medical devices through the network, a medical network system using the medical diagnostic apparatus, and a method of controlling the medical diagnostic apparatus.

2. Description of the Related Art

In recent years, an ultrasonic diagnostic apparatus and various medical devices are connected to each other through a hospital network, and there has been a system that controls services supported by various medical devices by using the ultrasonic diagnostic apparatus through the hospital network.

For example, such a system performs communication on the basis of a DICOM (Digital Image and Communications in Medicine) communication protocol after forming connection between the ultrasonic diagnostic apparatus and various medical devices through a TCP/IP (Transmission Control Protocol/Internet Protocol), and. Accordingly, confirmation of connected devices, image transfer, confirmation of image transfer storage, image film print, generation of inspection reservation information, inspection status notification have been required to be performed with high efficiency between the other apparatuses.

However, it is necessary that various parameters required to perform DICOM communication with the ultrasonic diagnostic apparatus between the various medical devices be set in the system, and most of the setting operation is manually performed by an operator of the ultrasonic diagnostic apparatus. For this reason, a lot of time and effort is necessary to set various parameters, and a setting miss or the like is occurred. Therefore, reliability of the setting parameters is reduced. In addition, operational load applied to the operator of the ultrasonic diagnostic apparatus is increased due to a fact that the operator should have knowledge on the TCP/IP communication or DICOM communication.

There has been proposed a system that controls a part of services, such as obtainment of diagnostic image data, corresponding to various medical devices by means of a general purpose personal computer (for example, JP-A-11-239165). In this case, even though the DICOM communication protocol is not used, it is possible to obtain the diagnostic image data by the personal computer and to refer the diagnostic image data.

However, infrastructures different from each other, such as DICOM communication infrastructure and non-DICOM communication infrastructure, need to be provided in the above-mentioned system. Accordingly, the structure of the system becomes large, thus increasing user's investment load.

BRIEF SUMMARY OF THE INVENTION

It is an object of the invention to provide a medical diagnostic apparatus, a medical network system, and a method of controlling the medical diagnostic apparatus having advantages in which information setting required to control the communication and services can be accurately performed without help of an operator in a short time so as to improve reliability of the information setting when communication and services are controlled on the basis of a medical communication protocol, thus significantly reducing operator's load.

The invention is configured as described below in order to achieve the above-mentioned object.

A medical diagnostic apparatus according to the invention is connected to a plurality of medical terminals each having functions to support medical services defined by medical communication protocols through a communication network, selectively sets parameter information required to control a medical service of an arbitrary medical terminal among the medical terminals in a communication processing unit, and can control the selected medical service on the basis of the parameter information set in the communication processing unit. The medical diagnostic apparatus includes control information communication means that sends control information of the medical communication protocol to the plurality of medical terminals through the communication network when the medical diagnostic apparatus is connected to the plurality of medical terminals, parameter specifying means that specifies parameter information corresponding to the medical services of the plurality of medical terminals on the basis of the control information sent by the control information communication means, and control means that sets the parameter information in the communication processing unit if necessary, when the parameter information is specified by the parameter specifying means. The control information of the medical communication protocol is required to request the medical service.

According to the above-mentioned configuration, when the medical diagnostic apparatus is connected to the plurality of medical terminals, control information required to request the medical services supported by the plurality of medical terminals is received by the plurality of medical terminals. Then, parameter information corresponding to the medical services supported by the plurality of medical terminals is determined on the basis of the communication results of the control information, and the determined parameter information is set in the communication processing unit if necessary.

Accordingly, processes, until information required to control the medical services is set, are automatically performed through the communication network without help of the operator. For this reason, the user of the medical diagnostic apparatus can correctly perform information setting required to control the communication or services in a short time. As a result, operational load is significantly reduced.

The medical diagnostic apparatus further includes memory means that stores identification information used to identify the plurality of medical terminals on the communication network. In this case, the control information communication means confirms the state of the communication with the each medical terminal on the basis of the identification information of the plurality of medical terminals stored in the memory means, and sends communication line opening requests defined by the medical communication protocols. Further, the control means determines information indicating a medical service supported by the each medical terminal and a transfer syntax indicating the details of the medical service as the parameter information on the basis of the responses to the communication line opening requests.

According to the above-mentioned configuration, the state of communication or connection between the medical diagnostic apparatus and each of the plurality of medical terminals is determined using the identification information of the medical terminals stored on a recording medium. In addition, a transfer syntax and information indicating a medical service of each medical terminal are determined. For this reason, it is possible to set parameter information corresponding to a medical service of each medical terminal by a simple procedure.

The control information communication device notifies the communication results of the control information to a user. According to the above-mentioned configuration, a user, that is, an operator of the medical diagnostic apparatus can confirm whether the plurality of medical terminals can communicate with the medical diagnostic apparatus. Further, when the plurality of medical terminals cannot communicate with the medical diagnostic apparatus, the user can understand the reasons why the plurality of medical terminals cannot communicate with the medical diagnostic apparatus.

The control means includes a recording unit that records the parameter information specified by the parameter specifying means on a recording medium, and a setting unit that manages the parameter information recorded on the recording medium for each medical service and selectively reads the parameter information on the basis of the requested service so as to set the parameter information in the communication processing unit.

According to the above-mentioned configuration, the parameter information recorded on the recording medium can be managed for each service. Accordingly, it is possible to specify the parameter information when a desired medical service is controlled. As a result, it is possible to easily select a service. Further, if the parameter information recorded on the recording medium is used, the medical services do not need to be requested whenever the medical services are controlled and it is possible to immediately control the medical services.

The recording means notifies parameter information of each medical terminal specified by the parameter specifying means to a user, and records the parameter information of a corresponding medical terminal on a recording medium when the user inputs a recording order on the basis of the notification of the parameter information.

According to the above-mentioned configuration, when a plurality of medical terminals support the same service, a user can determine independently whether information used to control a medical service needs to be set in each medical terminal. As a result, it is possible to set only information used to control a medical service that is actually required.

The control information communication means sequentially sends control information to the plurality of medical terminals on the basis of preset conditions.

According to the above-mentioned configuration, a user does not need to designate a medical terminal serving as a destination, and control information is automatically sent to all medical terminals connected to the communication network.

BRIEF DESCRIPTION OF THE SEVERAL VIEWS OF THE DRAWING

FIG. 2 is a block diagram showing the functional configuration of an ultrasonic diagnostic apparatus shown in FIG. 1.

FIG. 3A is a view showing an example of contents of a common system designing table shown in FIG. 1.

FIG. 3B is a view showing an example of contents of an intrinsic system designing table shown in FIG. 1.

FIG. 5 is a flowchart illustrating processes for controlling the ultrasonic diagnostic apparatus according to the embodiment of the invention.

FIG. 6 is a view showing a display example of the ultrasonic diagnostic apparatus according to the embodiment of the invention.

DETAILED DESCRIPTION OF THE INVENTION

Hereinafter, embodiments of the invention will be described in detail with reference to the drawings.

Figure 1:
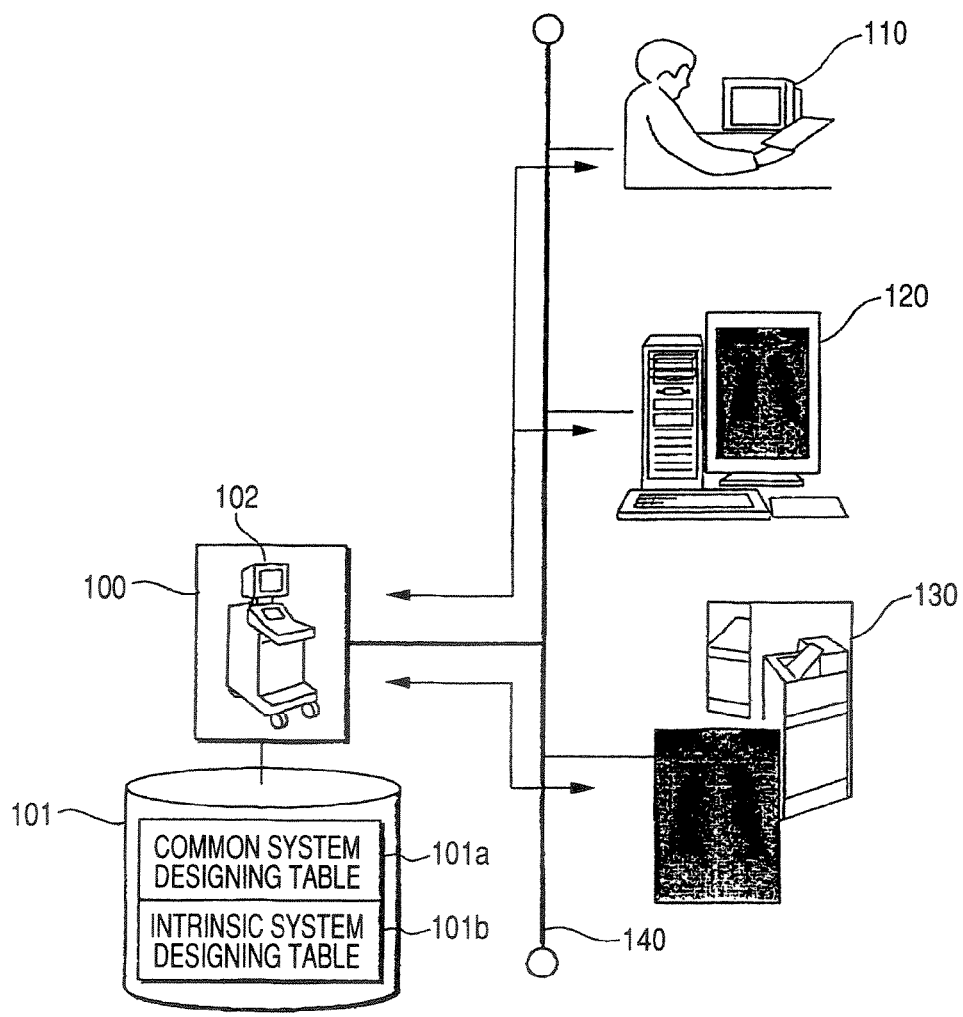
FIG. 1 is a schematic block diagram of a medical network system according to an embodiment of the invention.

FIG. 1 is a schematic block diagram of a medical network system according to an embodiment of the invention. In FIG. 1, reference numeral 100 denotes an ultrasonic diagnostic apparatus as a medical diagnostic apparatus, reference numeral 110 denotes an HIS (Hospital Information System)/RIS (Radiology Information System) server as a medical terminal, reference numeral 120 denotes a PACS (Picture Archivigand Communication System) server as a medical terminal, and reference numeral 130 denotes an imager as a medical terminal.

The ultrasonic diagnostic apparatus 100 is connected to a hospital network 140 that is a computer network provided in a facility such as a hospital. Further, the ultrasonic diagnostic apparatus 100 is to the HIS/RIS server 110, the PACS server 120, and the imager 130 through the hospital network 140.

A DICOM communication application is loaded in all of the ultrasonic diagnostic apparatus 100, the HIS/RIS server 110, the PACS server 120, and the imager 130.

The HIS/RIS server 110 generates inspection reservation information, and receives an inspection status notification. The PACS server 120 performs image transfer, image storage confirmation, and inspection search/reception. The imager 130 prints an image film.

The ultrasonic diagnostic apparatus 100 has a function to diagnose an object (to be inspected) by using an ultrasonic wave, as a basic function. Further, as shown in FIG. 2, the ultrasonic diagnostic apparatus 100 includes a TCP/IP information communication unit 100a, a DICOM information communication unit 100b, a service determining unit 100c, a parameter setting unit 100d, and a communication processing unit 100e. In addition, the ultrasonic diagnostic apparatus 100 is connected to a memory unit 101, and the memory unit 101 is provided with a common system designing table 101a and an intrinsic system designing table 101b.

As shown in FIG. 3A, the common system designing table 101a stores AE titles and port numbers defined by IP addresses and DICOM communication protocols of the HIS/RIS server 110, the PACS server 120, and the imager 130.

As shown in FIG. 3B, the intrinsic system designing table 101b stores abstract syntaxes and transfer syntaxes. The abstract syntaxes indicate contents of services that are supported by the HIS/RIS server 110, the PACS server 120, and the imager 130 so as to correspond to the AE titles. The transfer syntaxes indicate details (for example, uncompressed images and compressed images) of the services. For example, in case of the HIS/RIS server 110, the AE title is "RIS", the abstract syntax is "Modality worklist FIND", and the transfer syntax is "Implicit VR little endian". In case of the PACS server 120, the AE title is "Server", the abstract syntax is "Ultrasound image storage" or "Ultrasound Multi-frame image storage", and the transfer syntax is "Implicit VR little endian, Explicit VR little endian, and JPEG baseline process 1". In case of the imager 130, the AE title is "Imager", the abstract syntax is "Basic grayscale print management", and the transfer syntax is "Explicit VR little endian".

The TCP/IP information communication unit 100a sends TCP/IP communication ping commands to the HIS/RIS server 110, the PACS server 120, and the imager 130 through the hospital network 140 in a predetermined order on the basis of the common system designing table 101a provided in the memory unit 101, so as to confirm the connections of the HIS/RIS server 110, the PACS server 120, and the imager 130.

Figure 4:
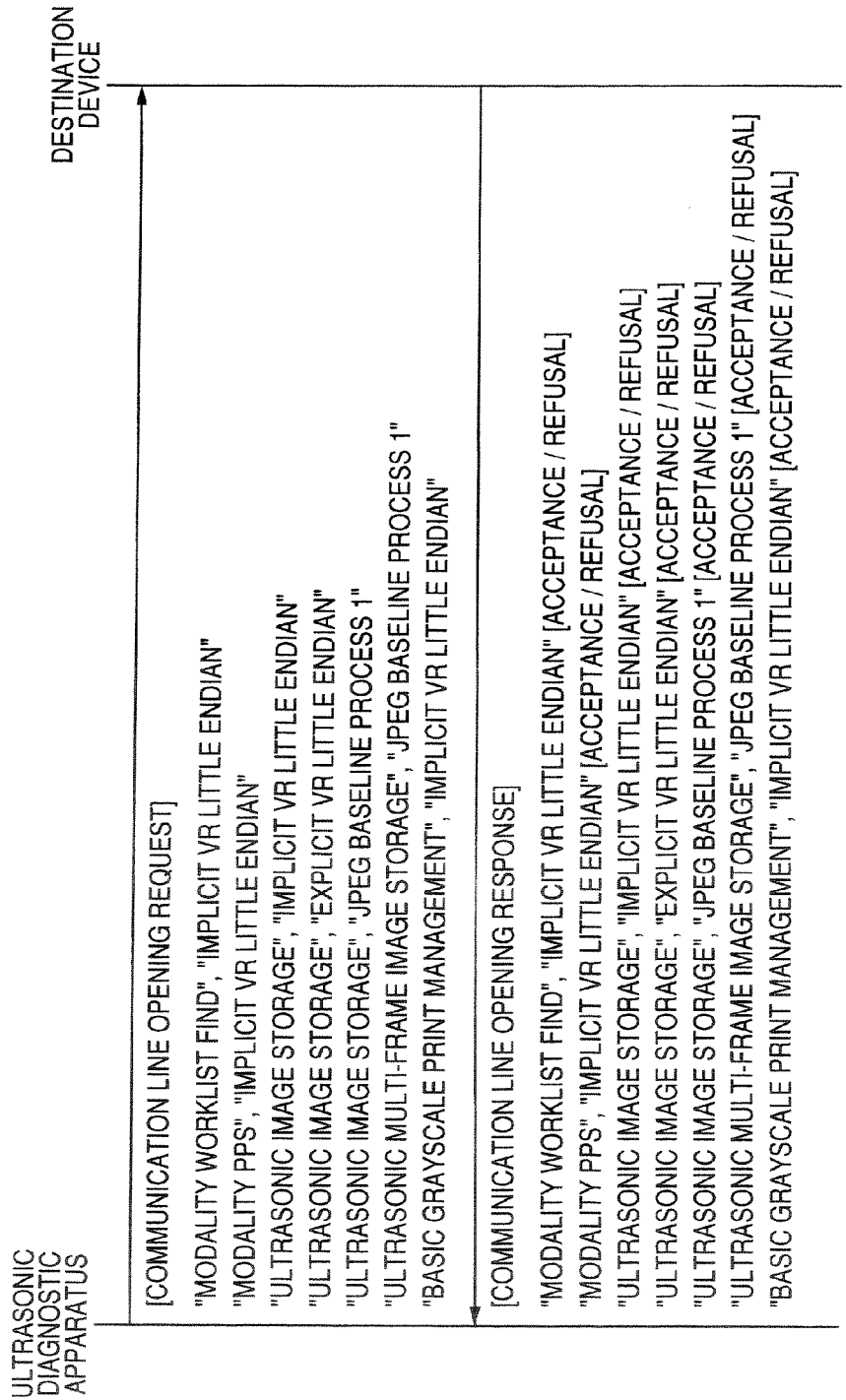
FIG. 4 is a sequence diagram illustrating a communicating operation between the ultrasonic diagnostic apparatus according to the embodiment of the invention and each destination.

As shown in FIG. 4, the DICOM information communication unit 100b sends communication line opening requests to the HIS/RIS server 110, the PACS server 120, and the imager 130, the connections of which are confirmed by the TCP/IP information communication unit 100a, through the hospital network 140 in a predetermined order. The communication line opening requests are formed by the combination of the abstract syntaxes and the transfer syntaxes about all DICOM services.

The service determining unit 100c determines a host name, an IP address, an AE title, a port number, an abstract syntax, and a transfer syntax, which are supported by each destination, on the basis of the responses from the HIS/RIS server 110, the PACS server 120, and the imager 130 to the communication line opening requests.

The parameter setting unit 100d displays the host name, the IP address, the AE title, the port number, the abstract syntax, and the transfer syntax, which are supported by each destination, on a monitor 102. The parameter setting unit 100d stores corresponding AE title, abstract syntax, and transfer syntax in the intrinsic system designing table 101b on the basis of a recording order input from a user, so as to manage them.

After that, the user of the ultrasonic diagnostic apparatus 100 performs an operation for requesting service controls on the basis of the AE title, the abstract syntax, and the transfer syntax of each destination, which are stored in the intrinsic system designing table 101b. As a result, corresponding host name, IP address, AE title, port number, abstract syntax, and transfer syntax are set as parameter information in the communication processing unit 100e of the ultrasonic diagnostic apparatus 100. Then, the control of the inspection status notification (DICOM MPPS service control), the control of the generation of the inspection reservation information (DICOM MWM service control) on the HIS/RIS server 110, the control of the image transfer (DICOM Strage service control), the control of confirming the images stored in the PACS server 120 (DICOM Strage Commitment service control), the control of performing the inspection search/reception on the PACS server 120, or the control of printing the image film to the imager 130 (DICOM Print service control) is performed on the basis of the parameter information.

The operation of the system configured as described above will be described below.

FIG. 5 is a flow chart illustrating control processes of the ultrasonic diagnostic apparatus 100 when the DICOM information is set up.

A user of the ultrasonic diagnostic apparatus 100 performs an operation for requesting information setting in order to use a DICOM service. Then, the ultrasonic diagnostic apparatus 100 starts the automatic setting of the DICOM information (Step ST4a), and it is determined whether setting items of the HIS/RIS server 110, the PACS server 120, and the imager 130 exist in the common system designing table 101a of the memory unit 101 (Step ST4b).

When the setting items exist (presence of the items), the ultrasonic diagnostic apparatus 100 sends TCP/IP communication ping commands to the HIS/RIS server 110, the PACS server 120, and the imager 130 through the hospital network 140 on the basis of the common system designing table 101a, so as to confirm the connections of the HIS/RIS server 110, the PACS server 120, and the imager 130 (Step ST4c).

When a connection error occurs (connection NG), the ultrasonic diagnostic apparatus 100 supplies a connection error message, corresponding host name, and corresponding IP address to the monitor 102 so as to display them (Step ST4d). Accordingly, the user can perceive the occurrence of the error through the display.

Meanwhile, when a connection error does not occur, the ultrasonic diagnostic apparatus 100 sends communication line opening requests to the HIS/RIS server 110, the PACS server 120, and the imager 130, the connections of which are confirmed, through the hospital network 140. The communication line opening requests are formed by the combination of the abstract syntaxes and the transfer syntaxes about all DICOM services. Then, the ultrasonic diagnostic apparatus 100 determines a host name, an IP address, an AE title, a port number, an abstract syntax, and a transfer syntax, which are supported by each destination, on the basis of the responses to the communication line opening requests (Step ST4e). In this case, even though a predetermined time passes, when the response is not returned or a connection error occurs, the ultrasonic diagnostic apparatus 100 performs the process of Step ST4d.

When the host name, the IP address, the AE title, the port number, the abstract syntax, and the transfer syntax that are determined by the ultrasonic diagnostic apparatus 100 are correct (OK), the ultrasonic diagnostic apparatus 100 displays the host name, the IP address, the AE title, the port number, the abstract syntax, and the transfer syntax on the monitor 102, as shown in FIG. 6 (Step ST4f). Accordingly, the user can check the host name, the IP address, the AE title, the port number, the abstract syntax, and the transfer syntax of each destination, which is connected to the hospital network 140, through the display.

Then, when the user selectively designates a host name, an IP address, an AE title, a port number, an abstract syntax, and a transfer syntax of a destination to be stored in the intrinsic system designing table 101b, the ultrasonic diagnostic apparatus 100 stores the host name, the IP address, the AE title, the port number, the abstract syntax, and the transfer syntax of each destination, which are selectively designated, in the intrinsic system designing table 101b (Step ST4g). After that, the ultrasonic diagnostic apparatus 100 manages an AE title, an abstract syntax, and a transfer syntax of each destination provided in the intrinsic system designing table 101b, and sets a host name, an IP address, an AE title, a port number, an abstract syntax, and a transfer syntax of corresponding destination as parameter information in the communication processing unit, depending on a service to be requested. Then, the ultrasonic diagnostic apparatus 100 performs service controls.

As described above, the user of the ultrasonic diagnostic apparatus 100 can use arbitrary DICOM services, which are supported by each destination, using the ultrasonic diagnostic apparatus 100 on the basis of an AE title, an abstract syntax, and a transfer syntax of each destination stored in the intrinsic system designing table 101b. For example, when the user designates the DICOM MWM service, the HIS/RIS server 110 generates inspection reservation information. When the user designates the DICOM Print service, the imager 130 prints an image film.

According to the above-mentioned embodiment, when the ultrasonic diagnostic apparatus 100 is connected to the HIS/RIS server 110, the PACS server 120, and the imager 130 through the hospital network 140, the state of the communication or connection with the HIS/RIS server 110, the PACS server 120, and the imager 130 is determined using information stored in the common system designing table 101*a* of the memory unit 101. In addition, the ultrasonic diagnostic apparatus 100 sends communication line opening requests for requiring supporting DICOM services to the HIS/RIS server 110, the PACS server 120, and the imager 130, and determines a transfer syntax and a DICOM service supported by each destination on the basis of the responses to the communication line opening requests, so as to store information in the intrinsic system designing table 101*b*.

Accordingly, processes, until information required to use the DICOM services is set, are automatically performed through the hospital network 140 without help of the operator. For this reason, the user of the ultrasonic diagnostic apparatus 100 can correctly perform information setting required to control the communication or services in a short time. As a result, operational load is significantly reduced. In addition, it is possible to appropriately determine a DICOM service of each destination by a simple procedure. As a result, it is possible to further improve the reliability of the service control.

Further, in the above-mentioned embodiment, since communication results of the TCP/IP communication ping commands or communication results of DICOM information that are communication line opening requests are displayed on the monitor 102, the user of the ultrasonic diagnostic apparatus 100 can confirm whether the HIS/RIS server 110, the PACS server 120, and the imager 130 can communicate with the ultrasonic diagnostic apparatus. When the HIS/RIS server 110, the PACS server 120, and the imager 130 can communicate with the ultrasonic diagnostic apparatus, the user can understand that the HIS/RIS server 110, the PACS server 120, and the imager 130 do not correspond to DICOM communication protocols, or reasons why troubles occur in the HIS/RIS server 110, the PACS server 120, and the imager 130.

Furthermore, in the above-mentioned embodiment, a host name, an IP address, an AE title, a port number, an abstract syntax, and a transfer syntax of each destination are displayed on the monitor 102 by the responses from the HIS/RIS server 110, the PACS server 120, and the imager 130, and are stored in the intrinsic system designing table 101*b* by a user's command. Accordingly, when a plurality of medical terminals for supporting the same service as the HIS/RIS server 110 are provided on the hospital network 140, a user can selectively designate the HIS/RIS server 110 and store information of the HIS/RIS server in the intrinsic system designing table 101*b*.

The invention is not limited to the above-mentioned embodiment. For example, a DICOM Verification service and a DICOM Query and Retrieve service may be supported by the HIS/RIS server 110, the PACS server 120, and the imager 130. For example, when the DICOM Verification service is selectively designated, the operational state of an apparatus is notified. When the DICOM Query and Retrieve service is selectively designated, the quality of the service is notified. Further, it is possible to also perform DICOM services other than a DICOM Verification service, a DICOM Storage service, a DICOM Storage Commitment service, a DICOM Query and Retrieve service, a DICOM Print service, a DICOM MWM service, and a DICOM MPPS service.

Furthermore, in the above-mentioned embodiment, the host name, the IP address, the AE title, the port number, the abstract syntax, and the transfer syntax of each destination are displayed on the monitor 102. When a user inputs the recording order, the AE title, the abstract syntax, and the transfer syntax of each destination are stored in the intrinsic system designing table 101*b*.

However, the invention is not limited thereto. That is, when the host name, the IP address, the AE title, the port number, the abstract syntax, and the transfer syntax of each destination are obtained, the AE title, the abstract syntax, and the transfer syntax of each destination may be stored in the intrinsic system designing table 101*b*.

The invention has been described with reference to the embodiment as described above. However, the invention is not limited to the embodiment. That is, when the invention is embodied, the invention may be embodied through the modification of components without departing from the scope of the invention. In addition, it is possible to form various inventions through the appropriate combination of the components disclosed in the embodiment. For example, some components may be removed from all components disclosed in the embodiment.

What is claimed is:

1. A medical diagnostic apparatus comprising:
   a connecting device that is connected to a plurality of medical terminals each having functions to support medical services defined by medical communication protocols through a communication network;
   a communication processing unit that selectively sets parameter information required to control a medical service of an arbitrary medical terminal among the medical terminals and can control the selected medical service on the basis of the parameter information; a control information communication device that sends control information of the medical communication protocol to the plurality of medical terminals through the communication network in response to the plurality of medical terminals being connected and a user of the medical diagnostic apparatus performing an operation for requesting setting of information in order to use the medical service, the control information of the medical communication protocol being required to request the medical service, wherein the plurality of medical terminals provide information in response to a receipt of the control information;
   a parameter specifying device that specifies parameter information corresponding to the medical services of the plurality of medical terminals on the basis of the control information sent by the control information communication device; and
   a control device that sets the parameter information in the communication processing unit if necessary, when the parameter information is specified by the parameter specifying device; and
   a memory device that stores identification information that identifies the plurality of medical terminals on the communication network,
   wherein when the medical communication protocol is a DICOM (Digital Image and Communications in Medicine) communication protocol, the control information communication device confirms a state of communication with each of the medical terminals on the basis of the identification information of the plurality of medical terminals stored in the memory device, and sends communication line opening requests for either a DICOM Verification service, a DICOM Storage service, a DICOM Storage Commitment service, a DICOM Query and Retrieve service, a DICOM Print service, a DICOM MWM (Modality Worklist Management) service, or a DICOM MPPS (Modality Performed Procedure Step) service, and the parameter specifying device specifies parameter information corresponding to at least one of the DICOM Verification service, the DICOM Storage service, the DICOM Storage Commitment service, the DICOM Query and Retrieve service, the DICOM Print service, the DICOM MWM service, and the DICOM MPPS service on the basis of the responses to the communication line opening requests.

2. The medical diagnostic apparatus according to claim 1, wherein the control information communication device notifies communication results of the control information to a user.

3. The medical diagnostic apparatus according to claim 1, wherein the control device includes a recording unit that records the parameter information specified by the parameter specifying device on a recording medium, and a setting unit that manages the parameter information recorded on the recording medium for each service and selectively reads the parameter information on the basis of the requested medical service so as to set the parameter information in the communication processing unit.

4. The medical diagnostic apparatus according to claim 3, wherein the recording unit notifies parameter information of each medical terminal specified by the parameter specifying device to a user, and records the parameter information of corresponding medical terminal on the recording medium when the user inputs a recording order on the basis of the notification of the parameter information.

5. The medical diagnostic apparatus according to claim 1, wherein the control information communication device sequentially sends the control information to the plurality of medical terminals on the basis of preset conditions.

6. A medical network system including a medical diagnostic apparatus that is connected to a plurality of medical terminals each having functions to support medical services defined by medical communication protocols through a communication network, selectively sets parameter information required to control a medical service of an arbitrary medical terminal among the medical terminals in a communication processing unit, and can control selected medical service on the basis of the parameter information set in the communication processing unit, the system comprising:

a control information communication device that sends control information of the medical communication protocol to the plurality of medical terminals through the communication network between the medical diagnostic apparatus and the plurality of medical terminals in response to the medical diagnostic apparatus being connected to the plurality of medical terminals and a user of the medical diagnostic apparatus performing an operation for requesting setting of information in order to use the medical service, the control information of the medical communication protocol being required to request the medical service supported by the plurality of medical terminals, wherein the plurality of medical terminals provide information in response to a receipt of the control information;

a parameter specifying device that specifies parameter information corresponding to the medical services of the plurality of medical terminals on the basis of the control information sent by the control information communication device; and a control device that sets the parameter information in the communication processing unit of the medical diagnostic apparatus if necessary, when the parameter information is specified by the parameter specifying device; and a memory device that stores identification information that identifies the plurality of medical terminals on the communication network, wherein when the medical communication protocol is a DICOM (Digital Image and Communications in Medicine) communication protocol, the control information communication device confirms a state of communication with each of the medical terminals on the basis of the identification information of the plurality of medical terminals stored in the memory device, and sends communication line opening requests for either a DICOM Verification service, a DICOM Storage service, a DICOM Storage Commitment service, a DICOM Query and Retrieve service, a DICOM Print service, a DICOM MWM (Modality Worklist Management) service, or a DICOM MPPS (Modality Performed Procedure Step) service, and the parameter specifying device specifies parameter information corresponding to at least one of the DICOM Verification service, the DICOM Storage service, the DICOM Storage Commitment service, the DICOM Query and Retrieve service, the DICOM Print service, the DICOM MWM service, and the DICOM MPPS service on the basis of the responses to the communication line opening requests.

7. A method of controlling a medical diagnostic apparatus that is connected to a plurality of medical terminals each having functions to support medical services defined by medical communication protocols through a communication network, selectively sets parameter information required to control a medical service of an arbitrary medical terminal among the medical terminals in a communication processing unit, and can control selected medical service on the basis of the parameter information set in the communication processing unit, the method comprising:

sending control information of the medical communication protocol to the plurality of medical terminals through the communication network in response to a connection being initiated with the plurality of medical terminals and an operation for requesting setting of information in order to use the medical service being performed by a user of the medical diagnostic apparatus, the control information of the medical communication protocol being required to request the medical service, wherein the plurality of medical terminals provide information in response to a receipt of the control information;

specifying parameter information corresponding to the medical services of the plurality of medical terminals on the basis of the control information to be sent; and setting the parameter information in the communication processing unit if necessary, when the parameter information is specified, storing identification information in a memory device that identifies the plurality of medical terminals on the communication network, wherein when the medical communication protocol is a DICOM (Digital Image and Communications in Medicine) communication protocol, a state of communication is confirmed with each of the medical terminals on the basis of the identification information of the plurality of medical terminals stored in the memory device, and communication line opening requests are sent for either a DICOM Verification service, a DICOM Storage service, a DICOM Storage Commitment service, a DICOM Query and Retrieve service, a DICOM Print service, a DICOM MWM (Modality Worklist Management) service, or a DICOM MPPS (Modality Performed Procedure Step) service, and parameter information corresponding to at least one of the DICOM Verification service, the DICOM Storage service, the DICOM Storage Commitment service, the DICOM Query and Retrieve service, the DICOM Print service, the DICOM MWM service, and the DICOM MPPS service is specified on the basis of the responses to the communication line opening requests.

* * * * *